(12) United States Patent
Aghion

(10) Patent No.: US 11,723,829 B2
(45) Date of Patent: *Aug. 15, 2023

(54) APPARATUS AND METHOD FOR TREATING TISSUE

(71) Applicant: LUMENIS LTD., Yokneam (IL)

(72) Inventor: Joseph Aghion, Yokneam Ilit (IL)

(73) Assignee: LUMENIS BE LTD., Yokneam (IL)

( * ) Notice: Subject to any disclaimer, the term of this patent is extended or adjusted under 35 U.S.C. 154(b) by 231 days.

This patent is subject to a terminal disclaimer.

(21) Appl. No.: 17/114,762

(22) Filed: Dec. 8, 2020

(65) Prior Publication Data

US 2021/0283004 A1    Sep. 16, 2021

Related U.S. Application Data

(63) Continuation of application No. 16/117,100, filed on Aug. 30, 2018, now Pat. No. 10,888,491, which is a continuation of application No. 14/823,016, filed on Aug. 11, 2015, now Pat. No. 10,085,911, which is a continuation of application No. 11/937,917, filed on Nov. 9, 2007, now Pat. No. 9,101,524.

(60) Provisional application No. 60/857,807, filed on Nov. 9, 2006.

(51) Int. Cl.
*A61H 7/00* (2006.01)
*A61N 1/40* (2006.01)
*A61N 5/06* (2006.01)

(52) U.S. Cl.
CPC .............. *A61H 7/008* (2013.01); *A61N 1/40* (2013.01); *A61N 5/0616* (2013.01); *A61H 2201/5071* (2013.01); *A61H 2201/5092* (2013.01)

(58) Field of Classification Search
CPC ............ A61H 7/008; A61H 2201/5071; A61H 2201/5092; A61N 1/40; A61N 5/0616
See application file for complete search history.

(56) References Cited

U.S. PATENT DOCUMENTS

| | | |
|---|---|---|
| 4,729,368 A | 3/1988 | Guitay |
| 5,665,053 A | 9/1997 | Jacobs |
| 5,674,191 A | 10/1997 | Edwards et al. |
| 5,885,232 A | 3/1999 | Guitay |
| 5,891,064 A | 4/1999 | Van Herk et al. |
| 5,935,088 A | 8/1999 | Bosley |
| 6,017,320 A | 1/2000 | Bleeker |
| 6,662,054 B2 | 12/2003 | Kreindel et al. |

(Continued)

FOREIGN PATENT DOCUMENTS

WO    199603959    2/1996

*Primary Examiner* — Quang D Thanh
(74) *Attorney, Agent, or Firm* — Isus Intellectual Property PLLC; Anthony Jason Mirabito

(57) ABSTRACT

An apparatus and method used for medical and/or cosmetic treatment of a tissue, such as skin tightening, skin laxity and/or wrinkle reduction and or other skin flaws, including an energy source, a vacuum chamber and rollers which may facilitate easy sliding of the apparatus from one treated area to another. The rollers may also prevent excessive friction of the skin during the treatment. The energy source can be configured to emit energy based on the position of the apparatus on the skin (i.e., the position of the rollers), as well as the pressure within the vacuum chamber. The vacuum level and energy emission can be changed or pulsed based on the treatment regime.

10 Claims, 4 Drawing Sheets

(56) References Cited

U.S. PATENT DOCUMENTS

| | | |
|---|---|---|
| 6,743,215 B2 | 6/2004 | Bernabei |
| 6,758,845 B1 | 7/2004 | Weckwerth et al. |
| 6,926,683 B1 | 8/2005 | Kochman |
| 7,771,374 B2 | 8/2010 | Slatkine |
| 7,843,029 B2 | 11/2010 | Anderson et al. |
| 7,955,262 B2 | 6/2011 | Rosenberg |
| 9,101,524 B2 * | 8/2015 | Aghion .................. A61N 1/40 |
| 10,085,911 B2 * | 10/2018 | Aghion ................ A61H 7/008 |
| 10,888,491 B2 * | 1/2021 | Aghion ................ A61H 7/008 |
| 2002/0147467 A1 | 10/2002 | Bernabel |
| 2004/0073079 A1 * | 4/2004 | Altshuler ............ A61B 18/203 |
| | | 600/1 |
| 2004/0220622 A1 | 11/2004 | Bernabel |
| 2004/0260210 A1 | 12/2004 | Ella et al. |
| 2005/0049543 A1 | 3/2005 | Anderson et al. |
| 2006/0235339 A1 * | 10/2006 | Naldoni ............... A61H 9/0078 |
| | | 601/2 |
| 2006/0259102 A1 | 11/2006 | Slatkine |
| 2007/0123807 A1 | 5/2007 | Applebaum |
| 2007/0173749 A1 | 7/2007 | Williams et al. |
| 2007/0198004 A1 * | 8/2007 | Altshuler ............ A61N 5/0616 |
| | | 606/9 |
| 2007/0225621 A1 | 9/2007 | Sebastian |
| 2008/0167585 A1 | 7/2008 | Khen |
| 2008/0183252 A1 | 7/2008 | Khen |

* cited by examiner

APPARATUS AND METHOD FOR TREATING TISSUE

CROSS-REFERENCE TO RELATED APPLICATIONS

This application is a continuation application of U.S. application Ser. No. 16/117,100, filed Aug. 30, 2018, which is a continuation application of U.S. application Ser. No. 14/823,016, filed Aug. 11, 2015, now U.S. Pat. No. 10,085,911, issued on Oct. 2, 2018, which is a continuation application of U.S. application Ser. No. 11/937,917, filed Nov. 9, 2007, now U.S. Pat. No. 9,101,524, issued on Aug. 11, 2015, which claims the benefit of U.S. Provisional Application No. 60/857,807 filed on Nov. 9, 2006. The complete disclosures of these applications are hereby incorporated by reference.

FIELD OF THE INVENTION

The present invention relates to an apparatus and method useful in cosmetic or medical treatment of tissue, in particular skin tissue.

BACKGROUND OF THE INVENTION

There are various methods for cosmetic or medical treating of tissue, for example, a skin tissue, for reduction of wrinkles, skin tightening and other undesirable skin flaws. Some of these methods may be invasive, dangerous, or painful.

One non-invasive apparatus for treatment of tissue applies suction to the skin to draw it into a chamber, where the skin is then treated with radio frequency (RF) energy via plate electrodes. However, in order to treat large areas, the device must be moved around the skin from area to area, which may be painful due to the friction, which may be aggravated by the suction. In order to solve this problem, it has been suggested to use a lotion to reduce friction; however, the lotion may be sucked into the device due to the suction and interfere with its electrical and/or mechanical operation. It would be advantageous to have a non-invasive method for destroying or modifying tissue, which is relatively easy, efficacious, and cost effective to apply, that solves this and other problems.

SUMMARY

In general, in an aspect, the invention provides an apparatus for treating areas of the skin including a vacuum chamber including an opening configured to face an area of skin, a vacuum pump configured to add and remove air to and from the vacuum chamber, two parallel rollers disposed in proximity to the opening of the vacuum chamber and configured to make contact with the skin, wherein the surface of at least one of the rollers is an electrical conductor, and the point of contact between each of the rollers and the skin inhibits air flow into and out of the vacuum chamber, and an RF energy source operably coupled to at least one of the rollers and configured to transmit RF energy to the at least one roller.

Embodiments of the invention may further include one or more of the following features. The surface of at least one of the rollers can include a conductor portion and a nonconductor portion. A pressure sensor 32 can be configured to sense the air pressure in the vacuum chamber. A system controller 40 can be operably connected to the pressure sensor and the RF energy source and can be configured to control amount of RF energy transmitted to the at least one roller based on the air pressure in the vacuum chamber. The surface of at least one roller can include protrusions. A timer 42 can be operably connected to the vacuum pump and the RF energy source. A position indicator 44 can be operably connected to at least one roller and can be configured to determine the rotation rate of the roller as the apparatus moves across the skin. A power controller 46 can be operably connected to the position indicator and the RF energy source, the power controller can be configured to increase the RF energy transmitted to the at least one roller based on the rotation rate of the roller. An optical sensor can be configured to sense movement of apparatus across the skin.

In general, in another aspect, the invention provides a method of treating skin including placing a vacuum chamber against the skin of a patient, wherein the vacuum chamber includes two parallel rollers configured to contact the skin and inhibit air flow into and out of the vacuum chamber as the vacuum chamber rolls across the skin, changing the air pressure inside the vacuum chamber, and providing energy to the skin through at least one roller.

Embodiments of the invention may include one or more of the following features. Providing energy to the skin can include providing energy through the at least one roller when the air pressure inside the vacuum chamber is less than a predefined value. Providing energy to the skin can include providing energy through the at least one roller after a predefined suction time lapses. Providing energy to the skin can include increasing the intensity of the provided energy during a decrease of air pressure in the vacuum chamber. Providing energy to the skin can include varying the intensity of the provided energy as the vacuum chamber rolls across the skin.

In general, in another aspect, the invention provides a system for treating skin with optical energy including a vacuum control device including a vacuum pump, a vacuum chamber with two parallel spaced rollers disposed at the opening of the chamber and configured to contact the skin, wherein the rollers inhibit air flow into and out of the vacuum chamber as the vacuum chamber is rolled on the skin, an optical energy source configured to emit optical energy onto the skin disposed within the vacuum chamber, and an optical control circuit operably connected to the optical energy source and the vacuum control device.

Embodiments of the invention may include one or more of the following features. The vacuum control device can include a position sensor connected to at least one roller and can be configured to detect the rotational position of the roller, wherein the rotational position can include a count of full rotations. The optical energy can be emitted based on the rotational position of the roller. The vacuum control device can include a pressure sensor in the vacuum chamber, and the optical energy can be emitted based on the pressure in the vacuum chamber. The optical energy source can be an intense pulsed light (IPL). The optical energy source can be a laser.

In general, in another aspect, the invention provides an apparatus for applying RF energy to the skin of a person including an RF energy source, and at least one roller coupled to the RF energy source, the roller including a circumferential surface disposed on the skin and configured to transfer RF energy to the skin. In an embodiment, a vacuum system including a vacuum pump can be configured to remove air from a vacuum chamber, wherein the at least one roller is disposed in proximity to an opening on the vacuum chamber, and a partial vacuum can be generated in the vacuum chamber when the opening and the at least one roller are applied to the skin. The at least one roller can include a conductive portion and a non-conductive portion.

In general, in another aspect, the invention provides an apparatus for applying optical energy to the skin including a roller device with at least two rollers spaced apart, each roller including a circumferential surface configured to be disposed on the skin, and an optical energy source disposed to transmit optical energy into the space between the rollers. In an embodiment, a control device can be operably connected to the roller device and can be configured to detect the motion of at least one roller, wherein the optical energy can be transmitted based on the motion of the at least one roller.

In accordance with implementations of the invention, one or more of the following capabilities may be provided. Electrical energy (e.g., RF and optical energy) can be applied to skin while the skin is being stretched in a vacuum chamber. The electrical energy can be based on pressure within the vacuum chamber. The vacuum chamber can be rolled along the skin. The rollers can act as electrodes. The position of the vacuum chamber and be recorded, and the electrical energy can be applied based on the position.

These and other capabilities of the invention, along with the invention itself, will be more fully understood after a review of the following figures, detailed description, and claims.

BRIEF DESCRIPTION OF THE FIGURES

The principles and operation of the system, apparatus, and method according to the present invention may be better understood with reference to the drawings, and the following description, it being understood that these drawings are given for illustrative purposes only and are not meant to be limiting, wherein:

FIG. 1 A is a schematic illustration of exemplary roller configurations;

Figure 1:
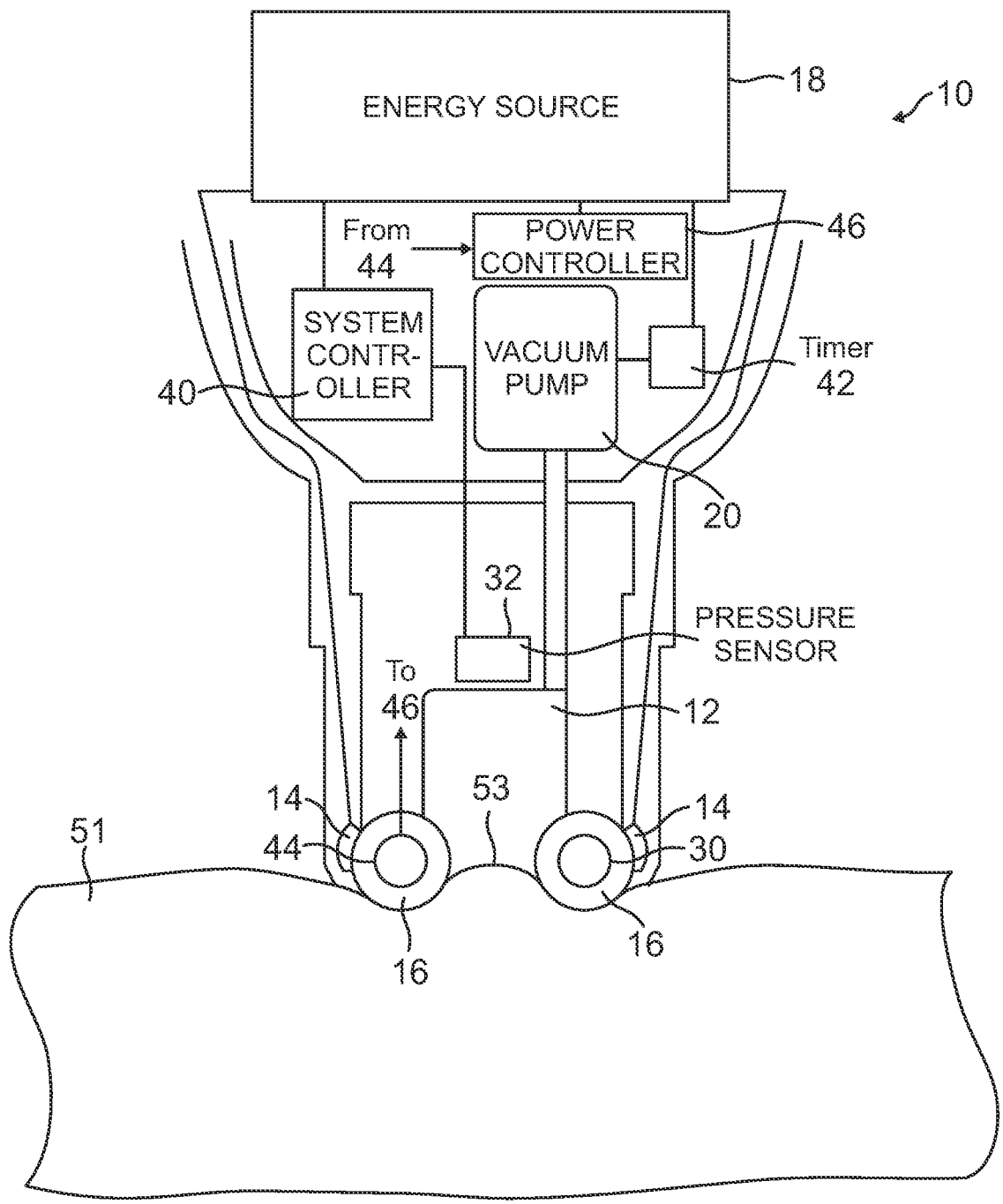
FIG. 1 is a schematic illustration of an apparatus according to one embodiment of the present invention.

It will be appreciated that for simplicity and clarity of illustration, elements shown in the drawings have not necessarily been drawn to scale. For example, the dimensions of some of the elements may be exaggerated relative to other elements for clarity. Further, where considered appropriate, reference numerals may be repeated among the drawings to indicate corresponding or analogous elements throughout the serial views.

DETAILED DESCRIPTION OF PREFERRED EMBODIMENTS

Embodiments of the invention provide techniques for treating of tissue. This treatment is exemplary, however, and not limiting of the invention as other implementations in accordance with the disclosure are possible.

An apparatus for treating tissue according to some embodiments of the present invention may comprise vacuum control device including a vacuum pump for changing air pressure in a chamber. The chamber may include at least one opening which may be placed, for example, on a treated tissue area. As the air pressure decreases, the treated tissue may be drawn into the chamber, for example, as a result of the pressure difference. The apparatus may include one or two or more rollers installed at the opening of the chamber. The rollers may rotate freely or substantially frictionlessly, such that when a force is applied to the apparatus, they rotate and the apparatus is moved along the treated tissue area. The rollers can be combined with a mechanical assembly configured to move the rollers inwards and outwards across the opening to provide a massaging motion to the tissue drawn into the chamber. A lotion dispenser can be attached to the chamber and configured to provide lotion to the tissue. For example, the lotion can be used to reduce friction, to reduce impedance (e.g., improve electrical coupling), to provide medicine (e.g., anesthesia, drug), cosmetic material, or other photoactive additives to the treatment area. The vacuum pump may provide pulses of air pressure having predefined period. The vacuum control device may provide pulses of air pressure having predefined shape.

An apparatus according to some embodiments of the present invention may further include an energy source, for example, an RF energy source. The energy source may provide energy to the rollers, for example, when the air pressure in the chamber is less than a predefined sufficient value, or after the lapse of a predefined time during which suction is applied. The rollers may be conductive. The rollers may, for example, conduct the provided energy to the treated tissue, thus, for example, provide heat to the treated tissue. The energy source may provide increasing energy intensity during decrease of the air pressure in the chamber, thus, for example, providing increasing heat to the treated tissue.

According to some embodiments, the apparatus may comprise at least two energy transmitting elements. The energy transmitting elements may transmit, for example, energy from the energy source to the rollers. The energy transmitting elements may enable energy transmission to the rollers during rotation, for example, without a fixed wire connection to the rollers. For example, the energy transmitting elements may be electrical brushes.

A method for treating tissue according to some embodiments of the present invention may include changing the air pressure inside a chamber. The method may further include, for example, providing energy to the treated tissue through at least one roller installed at an opening of the chamber, for example, when the air pressure in the chamber is less than a predefined value. The method may further include, for example, increasing intensity of the provided energy during decrease of the air pressure in the chamber. The method may further include, for example, sliding the apparatus on the treated tissue by rolling the rollers.

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

In the following detailed description, numerous specific details are set forth in order to provide a thorough understanding of the present invention. However, it will be understood by those skilled in the art that the present invention may be practiced without these specific details.

Embodiments of the present invention may provide an apparatus preferably used for medical and/or cosmetic treatment of a tissue, for example, for skin tightening, skin laxity and/or wrinkle reduction and or other skin flaws. Other conditions and tissues may be treated using embodiments of the present invention. The apparatus according to embodiments of the present invention enables treatment by using kneading, pressuring and/or stretching of the treated tissue, optionally combined with heat induced into the treated tissue, e.g., so as to modify, reduce or destroy undesirable cells in the treated tissue. Preferably, apparatus according to the present invention may include rollers which may facilitate easy sliding of the apparatus from one treated area to another. The rollers may also prevent excessive friction of the skin during the treatment.

Reference is now made to FIG. 1, which illustrates an apparatus 10 to enable treatment of tissue 51 according to one embodiment of the invention. Apparatus 10 may include a vacuum chamber 12 with a vacuum detection sensor. Pulses of changes in air pressure, e.g., vacuum pulses, may be delivered into vacuum chamber 12, for example by a vacuum pump 20. The vacuum pulses may, for example, effect kneading, pressuring and/or stretching of tissue 51. Drawing and/or expansion of a treated section 53 into vacuum chamber 12 may be effected, for example, when air is pumped out of vacuum chamber 12.

Apparatus 10 may further include rollers 16. Rollers 16 may, for example, facilitate drawing and/or expansion of treated tissue section 53 into vacuum chamber 12, thus, for example, preventing excessive friction or tearing of the skin when the apparatus is moved along the skin or when the skin is drawn into the vacuum chamber 12. Rollers 16 may enable easy sliding of apparatus 10 on the surface of tissue 51 from one section of tissue to another without removing apparatus 10 from tissue 51. Therefore, for example, the treatment of a large area may be continuous and uninterrupted. Rollers 16 may be installed, for example, in a way that seals vacuum chamber 12, for example, by inhibiting air-flow between vacuum chamber 12 and the air outside of the system of apparatus 10.

The rollers 16 can be disposed on springs and configured to close into (i.e., pinch) the area of tissue 53 drawn into the vacuum chamber 12. In an embodiment, the apparatus 10 include an electro-mechanical assembly configured to move the rollers 16 inward and outward across the opening of the vacuum chamber 12. The motion of the rollers 16 can be coordinated with the level of pressure within the vacuum chamber 12 to create a squeezing or massaging motion as the tissue 53 moves into and out of the vacuum chamber 12.

Figure 1A:
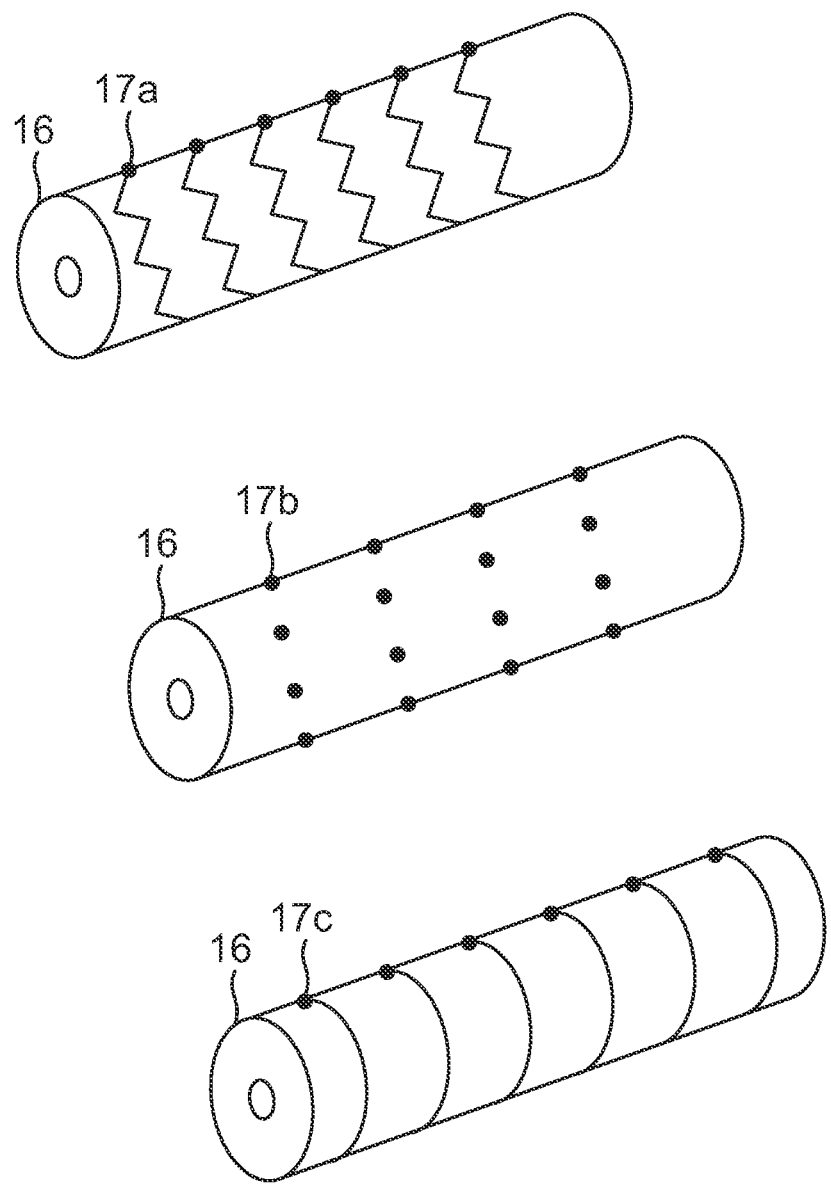

In some embodiments of the invention, the surface of the rollers may be partially non-conducting. For example, the rollers may be divided into sections, for example, two outer sections and an inner section. The outer sections, e.g., near the ends of the rollers, may have coating from rubber or another non-conducting material. In an embodiment, with reference to FIG. 1A, the rollers 16 include alternating bands of conducting 17a, b, c and non-conducting material configured to apply energy in patterns as the apparatus 10 is moved along the tissue 51. For example, the rollers 16 include conductive 17a, b, c material protruding up from on a non-conductive material in a fixed pattern, such as a herringbone, dots, or dashes. The relative size and location of the conductive and non-conductive materials can be varied based on the treatment regime. In an embodiment, the roller 16 is conductive and includes non-conductive protrusions 17a, b, c. In general, the roller materials can be high in friction when in contact with the skin, such that the device can roll with the skin, and not slip or slide thereupon. In another embodiment, the conducting portion of the rollers may not be entirely smooth, for example, they may have protrusions or the surface of the electrode may be roughened. As an example, and not a limitation protrusions include small teeth similar to a gear assembly spaced around the roller, scoring etched around the roller, bumps or small hollow needles (e.g., micro-fabricated micro needles) disposed on the roller.

Apparatus 10 may include, for example, an energy source 18, which may provide electrical energy to at least one of the rollers 16, for example, RF energy. The energy may be provided from energy source to rollers 16 via transmitting elements 14. Rollers 16 may conduct energy, for example, to provide heat to treated section 53. In an embodiment, energy is conducted through the conductive material 17a, b, c, disposed on the roller 16.

Energy transmitting elements 14 may enable energy transmission to rollers 16 during rotation of rollers 16, for example, without a fixed wire connection to rollers 16. For example, transmitting elements 14 may be electrical brushes or other contact-based electrical elements. As treated section 53 is expanded into vacuum chamber 12, the transmitted energy may affect deeper layers of treated section 53, which may include undesirable cells in the treated tissue. The intensity of the energy provided to rollers 16 may increase, for example, during increase of the vacuum level inside vacuum chamber 12, thus, for example, providing increasing heat to treated section 53 during drawing of treated section 53 into vacuum chamber 12 and therefore providing the highest level of energy when the deeper layers of the skin are affected by the energy. Alternatively, the intensity of the energy provided to rollers 16 may increase as function of the suction time. The energy may be provided to rollers 16 only after treated section 53 is sufficiently drawn and/or expanded into vacuum chamber 12. The heat gradient may be controlled by the system controller (not shown). Sufficient drawing and/or expansion may be ensured, for example, when the vacuum level is above a predefined sufficient vacuum level or after a predefined suction time lapses. The pulses of air pressure may be predefined and/or synchronized with the rotation of rollers 16 and/or with the energy transmission to rollers 16. Preferably, rollers 16 may comprise a material which may prevent skin burning. For example, rollers 16 may comprise conductors such as brass, stainless steel or aluminum, or combination thereof. In an embodiment, the rollers 16 include non-conducting material such as rubber, Teflon, and insulating oxide compositions.

In some embodiments of the invention, there may be a counter 30 attached to the axle of at least one of the rollers to count the number of rotations, and the device may thereby calculate the rate of rotation of the rollers. This may allow for varying the energy based on the movement or speed of the device. For example, the energy may be increased when the device is moving faster and decreased when the device is moving more slowly, in order to provide even exposure of the tissue to treatment. Additionally or alternatively, there may be an optical sensor to sense movement of the device across the skin. In some embodiments, there may be a memory to keep track of the location of the device based on its movement on the tissue.

Some embodiments of the invention may include an additional energy source (not shown), for example, an optical energy source, such as to emit intense pulsed light (IPL), laser, LED, or other optical energy, to treat skin drawn into the vacuum chamber.

Figure 2:
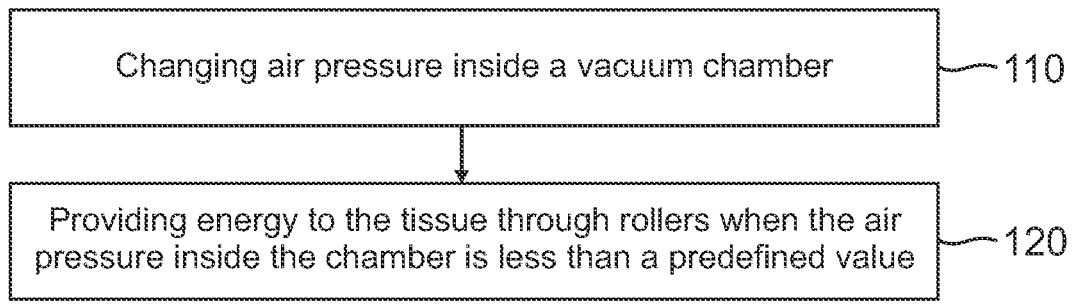
FIG. 2 is a flowchart describing steps of a method for treating tissue, according to some embodiments of the present invention.

Reference is made to FIG. 2, which is a flowchart describing steps of a method for treating tissue, according to some embodiments of the present invention. As indicated in block 110, the method may include changing the air pressure inside vacuum chamber 12, for example, decreasing the air pressure in the chamber. As indicated in block 120, the method may further include providing energy to tissue 51 through rollers 16, for example, when the air pressure inside vacuum chamber 12 is less than a predefined value.

Figure 3:
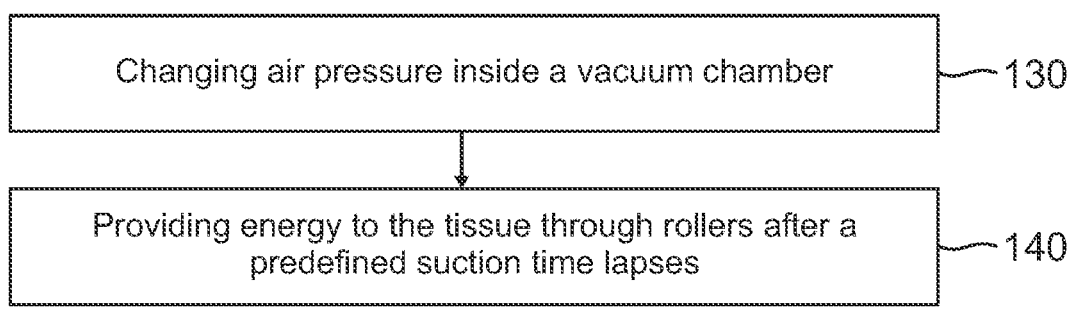
FIG. 3 is a flowchart describing steps of a method for treating tissue, according to other embodiments of the present invention.

Reference is now made to FIG. 3, which is a flowchart describing steps of a method for treating tissue, according to other embodiments of the present invention. As indicated in block 130, the method may include changing the air pressure inside vacuum chamber 12. As indicated in block 140, the method may include providing energy to tissue 51 through rollers 16, for example, after a predefined suction time lapses.

Figure 4:
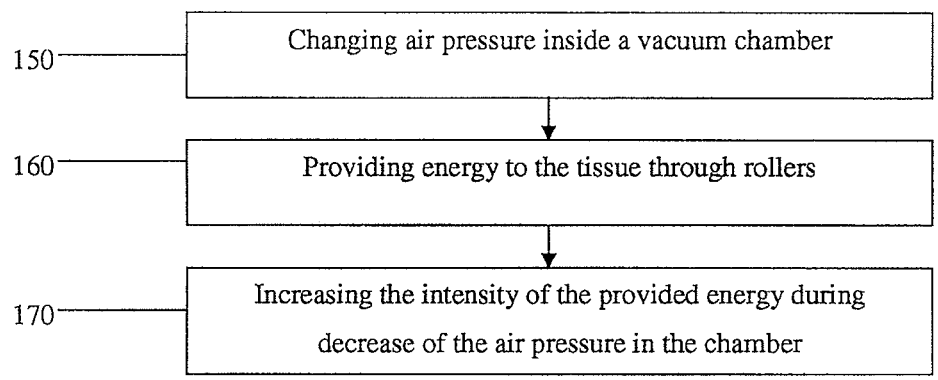
FIG. 4 is a flowchart describing steps of a method for treating tissue, according to other embodiments of the present invention.

Reference is now made to FIG. 4, which is a flowchart describing steps of a method for treating tissue, according to other embodiments of the present invention. As indicated in block 150, the method may include changing the air pressure inside vacuum chamber 12. As indicated in block 160, the method may include providing energy to tissue 51 through rollers 16. As indicated in block 170, the method may include increasing the intensity of the provided energy during decrease of the air pressure in vacuum chamber 12.

Figure 5:
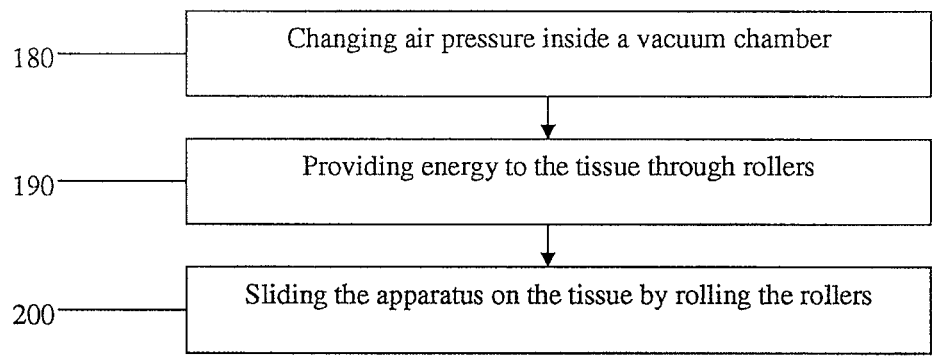
FIG. 5 is a flowchart describing steps of a method for treating tissue, according to other embodiments of the present invention.

Reference is now made to FIG. 5, which is a flowchart describing steps of a method for treating tissue, according to other embodiments of the present invention. As indicated in block 180, the method may include changing the air pressure inside vacuum chamber 12. As indicated in block 190, the method may include providing energy to tissue 51 through rollers 16. As indicated in block 200, the method may include sliding apparatus 10 on tissue 51 by rolling rollers 16, for example, in order to move apparatus 10 to another section of the treated tissue. Sliding the apparatus can include moving the rollers 16 in a pinching or massaging motion as energy is provided to the rollers 16.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

Further, while the description above refers to the invention, the description may include more than one invention.

What is claimed is:

1. An apparatus for treating areas of a skin of a person, comprising:
    a vacuum chamber including an opening configured to face an area of a skin surface;
    a vacuum pump configured to add and remove air to and from the vacuum chamber;
    two parallel, cylindrical rollers each disposed near opposing sides of the opening of the vacuum chamber and configured to make contact with the skin, at least a portion of at least one of the rollers including an electrical conductor;
    a radio frequency (RF) energy source configured to transmit an amount of RF energy from the at least one roller to the skin;
    an optical energy source configured to emit optical energy onto the skin disposed within the vacuum chamber;
    a pressure sensor configured to sense an air pressure in the vacuum chamber; and
    a system controller operably connected to the pressure sensor, the optical energy source and the RF energy source and configured to activate an application of RF energy transmitted to the at least one roller to the skin and to cause the optical energy source to emit the optical energy onto the skin based on the air pressure in the vacuum chamber;
    wherein, when the pressure sensor senses the air pressure inside the vacuum chamber at less than a predetermined value, the system controller causes the RF energy source to transmit the RF energy, and the optical energy source to emit the optical energy onto the skin; and
    wherein the optical energy source is at least one of an intense pulsed light (IPL), a laser and a light emitting diode (LED).

2. The apparatus of claim 1, wherein a surface of the at least one roller includes protrusions.

3. The apparatus of claim 1, further comprising a timer operably connected to the vacuum pump, the optical energy source and the RF energy source.

4. The apparatus of claim 1, further comprising: a position indicator operably connected to the at least one roller and configured to determine a rate of rotation of the at least one roller as the apparatus moves across the skin; and a power controller operably connected to the system controller and the position indicator and the RF energy source, the power controller being configured to vary the RF energy transmitted to the at least one roller based on the rate of rotation of the at least one roller.

5. The apparatus of claim 1 further comprising an optical sensor configured to sense movement of the apparatus across the skin.

6. The apparatus of claim 1 including a position indicator connected to the at least one roller and configured to detect a rotational position of the at least one roller, wherein the rotational position includes a count of full rotations.

7. The apparatus of claim 6 wherein the optical energy is emitted based on the rotational position of the at least one roller.

8. The apparatus of claim 1, wherein: the optical energy source disposed to transmit the optical energy into the opening of the vacuum chamber formed between the rollers.

9. The apparatus of claim 1, wherein the at least one roller including the electrical conductor includes both a conductor portion and a nonconductor portion comprising alternating bands of conducting and non-conducting material.

10. The apparatus of claim 4, wherein the motion of the rollers in contact with the skin is coordinated with an amount of pressure present within the vacuum chamber.

* * * * *